(12) United States Patent  (10) Patent No.: US 8,835,857 B2
Eggert  (45) Date of Patent: Sep. 16, 2014

(54) DEVICE FOR A RADIATION DETECTOR AND RADIATION DETECTOR WITH THE DEVICE

(75) Inventor: Tobias Eggert, Munich (DE)

(73) Assignee: Ketek GmbH, Munich (DE)

(*) Notice: Subject to any disclaimer, the term of this patent is extended or adjusted under 35 U.S.C. 154(b) by 55 days.

(21) Appl. No.: 13/571,193

(22) Filed: Aug. 9, 2012

(65) Prior Publication Data

US 2013/0037717 A1  Feb. 14, 2013

Related U.S. Application Data

(60) Provisional application No. 61/521,550, filed on Aug. 9, 2011.

(30) Foreign Application Priority Data

Aug. 9, 2011 (DE) .................. 10 2011 109 822

(51) Int. Cl.
G01T 1/20 (2006.01)
G01N 23/223 (2006.01)
G01T 7/00 (2006.01)

(52) U.S. Cl.
CPC .............. *G01T 7/00* (2013.01); *G01N 23/223* (2013.01)
USPC ............ 250/361 R; 250/363.01; 378/44; 378/45; 378/46; 378/53

(58) Field of Classification Search
CPC .............................. G01N 23/223; G01T 7/00
USPC ............... 250/361 R, 363.01; 378/44–46, 53
See application file for complete search history.

(56) References Cited

U.S. PATENT DOCUMENTS

| | | | | |
|---|---|---|---|---|
| 3,925,678 | A * | 12/1975 | Eberspaecher et al. | 378/156 |
| 3,963,922 | A * | 6/1976 | Zulliger et al. | 378/45 |
| 4,519,092 | A * | 5/1985 | Albert | 378/45 |
| 2003/0048877 | A1 * | 3/2003 | Price et al. | 378/203 |
| 2004/0011963 | A1 * | 1/2004 | Rodricks | 250/370.09 |
| 2008/0013681 | A1 | 1/2008 | Fukai et al. | |
| 2013/0279654 | A1 * | 10/2013 | Kantonen et al. | 378/49 |
| 2013/0284886 | A1 * | 10/2013 | Cook | 250/208.1 |

OTHER PUBLICATIONS

Ehrhardt, H., "X-ray fluorescence analysis use in enterprise laboratories," VEB Deutscher Verlag fur Grundstoffindustrie, Leipzig, 1981, 8 pages.
Henke, B.L., et al., "X-ray Interactions: Photoabsorption, Scattering, Transmission, and Reflection at E=50-30,000 eV, Z=1-92," Atomic and Nuclear Data Tables, vol. 54, No. 2, Jul. 1993, pp. 181-342.

* cited by examiner

*Primary Examiner* — David Porta
*Assistant Examiner* — Jeremy S Valentiner
(74) *Attorney, Agent, or Firm* — Slater & Matsil, L.L.P.

(57) ABSTRACT

A device for a radiation detector includes a main body, which includes a material G and is at least partially provided with a coating. The coating has at least a first layer with a material $A_1$. The material G of the main body can be excited by a primary radiation impinging on the coating, so that an x-ray fluorescence radiation is produced with an x-ray fluorescence spectrum, which has a maximum $M_G$ at an energy $E_G$. Furthermore, at an energy $E_1$, the material $A_1$ has an absorption edge. In this case, the material $A_1$ is chosen such that the relationships $E_1 < E_G$ and $E_G - E_1 \leq 4$ keV apply. Also specified is a radiation detector, which has the device and a detector element, which is suitable for the detection of the primary radiation.

22 Claims, 6 Drawing Sheets

|   |            | A        | B              | C              | D              | E              | F              | G              |
|---|------------|----------|----------------|----------------|----------------|----------------|----------------|----------------|
|   |            | E (eV)   | abs. Element   | λ(E) (μm)      | 2λ(E) (μm)     | 6λ(E) (μm)     | 12λ(E) (μm)    | 20λ(E) (μm)    |
| 1 | $E_{Ni,Max}$ | 8264   | Cr             | 6,08           | 12,16          | 36,47          | 72,94          | 121,57         |
| 2 | $E_{Ni}$   | 7477     | Cr             | 4,68           | 9,35           | 28,06          | 56,12          | 93,54          |
| 3 | $E_{Cr,Max}$ | 5946   | Ti             | 4,84           | 9,68           | 29,03          | 58,05          | 96,76          |
| 4 | $E_{Cr}$   | 5414     | Ti             | 3,81           | 7,63           | 22,89          | 45,77          | 76,29          |
| 5 | $E_{Ti,Max}$ | 4931   | Al             | 19,11          | 38,22          | 114,65         | 229,30         | 382,16         |
| 6 | $E_{Ti}$   | 4510     | Al             | 14,82          | 29,63          | 88,89          | 177,79         | 296,31         |

DEVICE FOR A RADIATION DETECTOR AND RADIATION DETECTOR WITH THE DEVICE

This application claims the benefit of U.S. Provisional Application No. 61/521,550, filed on Aug. 9, 2011, and German Patent Application No. 10 2011 109 822.8, filed Aug. 9, 2011, each of which is incorporated herein by reference in its entirety.

TECHNICAL FIELD

A device for a radiation detector is specified. Also specified is a radiation detector which has such a device.

Radiation detectors often have a protective cap, which is intended to protect a signal-generating detector element and possibly further elements of the radiation detector from external mechanical damage and often to serve at the same time as a mount for a radiation entrance window. Such a protective cap with a window mount and a window makes it possible for the detector to be hermetically sealed. Sealing of the detector is necessary, for example, if the detector element is cooled and is not operated in a vacuum or under a shielding gas atmosphere, since otherwise air moisture would condense on the cool detector chip and thus destroy the detector. Cooling of the detector element is often expedient to reduce leakage flows, and consequently noise.

With a radiation detector, it is often not possible to avoid the situation where the radiation that is to be detected reaches not only the detector element but also the window mount and the protective cap which surround the detector element.

High-energy photons and ionizing particles, such as for example electrons or alpha particles, may in principle induce at these locations x-ray fluorescence radiation, which is likewise measured by the radiation detector, thereby falsifying the measurement result. Such falsification of the measurement takes place, for example, if the energy of the interfering fluorescence radiation is in the energy range of the radiation to be detected by the detector. Since on the one hand protective caps and window mounts are usually composed of one or more metals and on the other hand measuring the x-ray fluorescence radiation of metals as samples is a frequent area of use of radiation detectors, such a configuration usually has interfering effects.

At present, therefore, external shieldings, which are intended to reduce the radiation that is incident on the protective cap and the window mount, are often used. In this case, however, the external shielding is excited and in turn emits secondary radiation. Although there is potentially the possibility here to choose the material according to the application such that the secondary radiation lies outside the measuring range, external shieldings nevertheless require additional expenditure and have the effect that the distance between the radiation source and the detector is increased, whereby the detection rate is reduced and the measuring time is prolonged.

SUMMARY OF THE INVENTION

Embodiments of the invention specify a device for a radiation detector. Other embodiments is to specify a radiation detector which has such a device. These embodiments and others are described hereafter. As such, advantageous embodiments and developments of the subjects become apparent from the description that follows and the drawings.

A device for a radiation detector is specified, comprising a main body which comprises a material G or consists of a material G. According to a first embodiment, the main body is at least partially provided with a coating. For example, the main body is coated with one or more layers, at least in partial regions.

According to a further embodiment, the coating has at least a first layer, the first layer comprising a material $A_1$. Particularly if it has two or more layers, the coating may also be referred to hereafter as a multilayer system.

The material G can be excited by a primary radiation impinging on the coating, so that it produces an x-ray fluorescence radiation with an x-ray fluorescence spectrum. The x-ray fluorescence spectrum in this case preferably has a maximum $M_G$ at an energy $E_G$. The maximum $M_G$ may be a local maximum or a global maximum in the x-ray fluorescence spectrum. For example, the maximum $M_G$ may be perceived as a x-ray fluorescence line in the x-ray fluorescence spectrum. For example, the x-ray fluorescence line in the x-ray fluorescence spectrum is a K line of G, such as for instance the $K_\alpha$ line of G, or an L line or M line of G, such as for example the $L_\alpha$ or $M_\alpha$ line. This x-ray fluorescence line may be the primary x-ray fluorescence line or else the primary line of G. In the x-ray fluorescence spectrum, the primary line may refer particularly to the line which has the maximum with the highest intensity. Preferably, the maximum $M_G$ is significantly different from the surroundings of the x-ray fluorescence line. For example, the maximum $M_G$ is higher than the average background in its surroundings by at least 20%, preferably at least 50%.

Furthermore, at an energy $E_1$, the material $A_1$ of the first layer has an absorption edge. The term absorption edge may refer to an abrupt drop in the absorption length of an element or a compound. The drop may occur, for example, when the irradiated energy corresponds exactly to the energy required to excite or ionize $A_1$. Sometimes the absorption coefficient, which corresponds to the inverse of the absorption length, is also used to characterize the absorption.

According to a further embodiment, the material $A_1$ is chosen such that $E_1 < E_G$. In terms of energy, the absorption edge of the material $A_1$ therefore preferably lies below, particularly just below, the energy of the x-ray fluorescence line of the material G that is to be suppressed. As a result, interfering x-ray fluorescence lines of the material G of the main body of the device can be advantageously suppressed by x-ray fluorescence radiation that is emitted by the material G being absorbed for the most part in the first layer.

According to a further embodiment, the material $A_1$ of the first layer is chosen such that the relationship $E_G - E_1 \leq 4$ keV applies. According to a further preferred embodiment, the material $A_1$ is chosen such that the relationship $E_G - E_1 \leq 3$ keV applies. According to a further, particularly preferred embodiment, the material $A_1$ is chosen such that the relationship $E_G - E_1 \leq 1$ keV applies. It has been found that, by coating the main body with a layer which comprises a material $A_1$ of which the absorption edge lies at an energy $E_1$ which is just below the energy $E_G$ of the x-ray fluorescence line of the material G of the main body that is to be suppressed, the interfering x-ray fluorescence line of the material G can be suppressed particularly efficiently.

According to a further embodiment, the first layer has a thickness $d_{A,1}$. Furthermore, at the energy $E_G$, the material $A_1$ has an absorption length $\lambda_{A,1}(E_G)$. The absorption length refers to that path length that a radiation must cover during the absorption in a medium until its intensity has fallen to a fraction 1/e of the incident intensity, where e is the Euler number. The absorption length may depend not only on the chemical element and on the excitation energy, but also on the density of the material and on the angle of incidence of the incident radiation. In case of doubt, it is assumed here that it is the absorption length which is determined with perpendicularly incident radiation and with a density of the material at 0° C. and with a pressure of 101 Pa. Furthermore, on the subject of absorption lengths, you are also referred to the following literature: B. L. Henke, E. M. Gullikson, J. C. Davis, X-ray interactions: photoabsorption, scattering, transmission, and reflection at E=50-30000 eV, Z=1-92, Atomic Data and Nuclear Data Tables, Vol. 54 (no. 2), 181-342 (July 1993). In particular as far as absorption lengths are concerned, the disclosure content of this publication is explicitly included in the present application by reference back to it.

The degree of absorption of radiation of the energy $E_G$ in the material $A_1$ can be determined by the equation $(1-\exp(-d_{A,1}/\lambda_{A,1}(E_G)))$. In order to suppress interfering x-ray fluorescence lines of the material G, the material $A_1$ of the first layer should therefore have an absorption length which is as short as possible for the energy $E_G$ of the x-ray fluorescence radiation of the material G. Preferably, the thickness $d_{A,1}$ of the first layer is chosen such that $d_{A,1} > \lambda_{A,1}(E_G)$ applies. Particularly preferably, the thickness $d_{A,1}$ is chosen such that $d_{A,1} > 2\lambda_{A,1}(E_G)$ applies. With such a choice of the layer thickness, the x-ray fluorescence radiation of the material G can be suppressed by at least 86%, that is to say at least 86% of the x-ray fluorescence radiation of the material G is absorbed in the first layer.

According to a further embodiment, as an alternative or in addition to the above embodiment, the thickness $d_{A,1}$ is chosen such that $d_{A,1} < 20\lambda_{A,1}(E_{G;\,Max})$ applies, where $\lambda_{A,1}$ is the energy-dependent absorption length of the material $A_1$ and $E_{G;\,Max}$ is the greatest energy, at which the x-ray fluorescence spectrum of the material G has a maximum. According to a further, preferred embodiment, the thickness $d_{A,1}$ is chosen such that $d_{A,1} < 12\lambda_{A,1}(E_{G;\,Max})$ applies. According to a further, particularly preferred embodiment, the thickness $d_{A,1}$ is chosen such that $d_{A,1} < 6\lambda_{A,1}(E_{G;\,Max})$ applies. Such limitations of the thickness $d_{A,1}$ allow the probability that the first layer is for its part excited by incident radiation and in turn emits interfering x-ray fluorescence radiation to be minimized. Particularly relevant for this interfering x-ray fluorescence radiation is not the primary line, but the x-ray fluorescence line with the highest energy $E_{G;\,Max}$ that the material G emits. This is often the $K_\beta$ or $L_\gamma$ line.

According to a further embodiment, the energy $E_{G;\,Max}$ is greater than the energy $E_G$.

According to a further, particularly preferred embodiment, the thickness $d_{A,1}$ is chosen such that the relationship $2\lambda_{A,1}(E_G) < d_{A,1} < 12\lambda_{A,1}(E_{G;\,Max})$ applies. It has been found that, with such a choice of the layer thickness, on the one hand particularly good suppression of the interfering x-ray fluorescence line of the material G takes place, and on the other hand only comparatively minimally interfering x-ray fluorescence radiation is emitted by the first layer, comprising the material $A_1$.

The material G and the material $A_1$ are preferably chemical elements. Preferably, the atomic number of the chemical element $A_1$ is less than the atomic number of the chemical element G. This is of advantage, since elements with a lower atomic number generally have a lower fluorescence yield and it is desirable that the element of the material $A_1$ of the first layer has a lower probability of renewed x-ray fluorescence than the element G. With lighter elements there is a higher probability of Auger electrons being generated instead of x-ray radiation.

It is often not possible to avoid completely the situation where the material $A_1$ of the first layer arranged on the main body G, excited by the x-ray fluorescence radiation of the main body, likewise emits x-ray fluorescence radiation, since there are no solid bodies that do not emit any x-ray fluorescence radiation under corresponding excitation. In order likewise to suppress the x-ray fluorescence radiation of the material $A_1$, a second layer, which comprises the material $A_2$ or consists of the material $A_2$, is applied to the first layer. The material $A_2$ preferably has an absorption edge which lies just below the primary line of the material $A_1$. According to one embodiment, the difference between the energies of the primary line of the material $A_1$ and the absorption edge of the material $A_2$ is less than or equal to 4 keV, according to a preferred embodiment less than or equal to 3 keV, and according to a particularly preferred embodiment less than or equal to 1 keV.

In the same way, a further, third layer, which comprises the material $A_3$ or consists of the material $A_3$, may be applied to the second layer, the third layer absorbing x-ray fluorescence radiation which is produced in the second layer, and so on. Although the outermost layer of the coating, furthest away from the main body G, will in principle likewise emit fluorescence radiation, because of the prior absorptions the intensity thereof is massively reduced, since the fluorescence yield is very low, particularly in the case of elements with a low atomic number.

According to a further embodiment, the coating has a number i of layers, which respectively comprise a material A, and have a thickness $d_{A,i}$, where i=2 to N, preferably N≥2 and/or N≤10. In this case, the ith layer is arranged directly on the (i-1)th layer. Furthermore, each layer i preferably comprises or consists of a material $A_i$, which is different from the material $A_{i-1}$ of the layer lying thereunder. Furthermore, the relationship $\lambda_{A,i}(E_{A,i-1}) < d_{A,i} < 20\lambda_{A,i}(E_{A,i-1;\,Max})$ should apply. Here, $\lambda_{A,i}$ is the energy-dependent absorption length of the material $A_i$, and the x-ray fluorescence spectrum of the material $A_{i-1}$ has a maximum at an energy $E_{A,i-1}$, and $E_{A,i-1;\,Max}$ is the greatest energy, at which the x-ray fluorescence spectrum of the material $A_{i-1}$ has a maximum. According to a further embodiment, the relationship $\lambda_{A,i}(E_{A,i-1}) < d_{A,i} < 12\lambda_{A,i}(E_{A,i-1;\,Max})$ applies. According to a further, preferred embodiment, the relationship $\lambda_{A,i}(E_{A,i-1}) < d_{A,i} < 6\lambda_{A,i}(E_{A,i-1;\,Max})$ applies. Instead of the specified lower limit, twice the value of the specified lower limit may also be set as the lower limit of the specified range. As a result, a multilayer system which suppresses interfering x-ray fluorescence radiation in an effective way can be advantageously produced.

According to a further embodiment, the energy at which the material $A_1$ has an absorption edge is less than the energy $E_{A,i-1}$ at which the x-ray fluorescence spectrum of the material $A_{i-1}$ has a maximum.

The same considerations as for the main body and the first layer may apply to all further layers that are arranged on the first layer of the coating—possibly with the exception of the outermost layer—and with the proviso that the further layers can be excited not only by the incident primary radiation, like the main body, but also by the x-ray fluorescence radiation which is produced in the layer lying respectively thereunder, so that the further layers are formed with the material $A_i$ in dependence on the characteristic energies—$E_{A,i-1}$ and $E_{A,i-1;\,Max}$ of the x-ray fluorescence spectrum of the material $A_{i-1}$ of the layer lying thereunder and possibly the energy of the absorption edge of the material $A_i$.

According to a further embodiment, each material $A_i$ is a chemical element $B_i$ the atomic number of the chemical element $B_i$ being less than the atomic number of the chemical element $B_{i-1}$. The material $A_2$ of a second layer is preferably therefore in turn chosen such that its atomic number lies below that of the material $A_1$ of the layer lying thereunder.

According to a further embodiment, the materials G and $A_i$ are solid bodies.

According to a further embodiment, the material G of the main body and the material $A_i$ (i=1 to N) of the respective layer of the coating, possibly with the exception of the uppermost layer, furthest away from the main body, respectively comprise chemical elements with an atomic number greater than 10.

According to a further embodiment, the material G of the main body and the material $A_i$ (i=1 to N) of the respective layer of the coating, possibly with the exception of the uppermost layer, respectively comprise or consist of chemical elements with a purity greater than 99.0%. The individual layers of the multilayer system may, for example, be produced by means of cathode sputtering. In this case, very pure cathodes of the respective element are respectively used.

According to a further, particularly preferred embodiment, the material G of the main body and the material $A_i$ (i=1 to N) of the respective layer of the coating respectively comprise chemical elements with an atomic number greater than 10 and with a purity greater than 99.0%. It has been found that a coating that meets these conditions can achieve particularly efficient suppression of undesired x-ray fluorescence radiation.

According to a further embodiment, the coating has at least two layers, the uppermost layer, furthest away from the main body, of the coating comprising a chemical element with an atomic number less than 10 and a purity less than 99.0%. If a material which consists of at least one chemical element with an atomic number less than 10 is used for the uppermost layer, it may also be a material with a lower purity than 99%, since these light elements have a very low fluorescence yield and, with light elements, the detector element has a lower quantum efficiency.

According to a further embodiment, the primary radiation comprises photons and/or ionizing particles. For example, the primary radiation may be an x-ray radiation. X-ray radiation may be used as a term to refer to electromagnetic radiation with a wavelength of approximately 15 nm (about 25 eV) to approximately 10 pm (approximately 124 keV). Furthermore, the primary radiation may also be alpha and/or beta and/or x-ray radiation.

According to a further embodiment, the device is formed as a window mount. The main body of the window mount preferably has a projection which serves for the fastening of a window. The projection may, for example, protrude from the main body into a free space formed by the main body inside the main body. Furthermore, it is expedient that the main body is stable enough to hold the window, and is suitable for allowing itself to be reliably connected to the window.

According to a further embodiment, the window comprises a material or consists of a material which has a coefficient of thermal expansion that corresponds substantially to the coefficient of thermal expansion of the material G of the main body of the device. Preferably, the coefficient of thermal expansion of the two materials should differ by a maximum of 100%. This proves to be of advantage in particular if the device is exposed to high temperature differences. With brazed beryllium windows, for example, nickel may be used as the material G of the main body.

Preferably, at least part of the surface of the projection is free from the coating. Preferably, the coating is not in the region of the projection where the window is connected to the projection, since the window can generally only be connected in a gastight and stable manner to the material G of the main body. The main body is preferably self-supporting, unsupported, dimensionally stable and/or capable of directly bearing loads. On the other hand, the coating, or at least part of the coating, cannot be unsupported and/or cannot be self-supporting.

According to a further embodiment, the device is formed as a cap for a radiation detector. Preferably, the device defines a cavity which has exposed inner surfaces which are at least partially provided with the coating. This allows x-ray fluorescence radiation which occurs in this region of the main body to be suppressed effectively.

According to a further embodiment, a window mount with at least one fastening region for the fastening of a window is provided in the cap, the fastening region being free from the coating. Preferably, regions of the window mount and/or of the cap that are adjacent to the fastening region are provided with the coating, so that undesired fluorescence radiation can be suppressed particularly well. Since with cathode sputtering each material is in principle deposited everywhere, either regions that are not intended to be coated should be masked before the cathode sputtering or the material must be removed again subsequently.

Also specified is a radiation detector which has a device described here and a detector element which is suitable for the detection of the primary radiation. The energy of the radiation must be so high that it is capable of causing x-ray fluorescence. This is the case, for example, if charged particles, for example electrons, alpha particles or heavy ions, or photons have an energy greater than 55 eV, since this energy is required to ionize the K shell of lithium, which is the lightest element that can emit x-ray fluorescence radiation. Furthermore, the radiation detector is preferably designed such that under incident radiation it generates a desired signal.

According to a further embodiment, the layer of the coating that is applied to the device and is furthest away from the main body comprises a material with an x-ray fluorescence spectrum which has a maximum at an energy which lies outside an energy range that is detectable or can be detected by the radiation detector, in particular by the detector element.

Furthermore, a material which has an x-ray fluorescence line which is not considered to be interfering in the application may be chosen for the layer of the coating that is applied to the device and furthest away from the main body. For example, the radiation detector has a window transparent to the primary radiation, the window being fastened to the device and comprising a material which corresponds to the material of the layer of the coating that is applied to the device and is furthest away from the main body. Usually, in this case the fluorescence radiation emitted by the material of this uppermost layer is not considered to be excessively interfering in the application.

BRIEF DESCRIPTION OF THE DRAWINGS

Further advantages and advantageous embodiments of the device described here and of the radiation detector described here become apparent from the embodiments described below in conjunction with FIGS. 1a to 5.

In the exemplary embodiments and figures, component parts that are the same or have the same effect can be respectively provided with the same designations. The elements represented and the sizes thereof in relation to one another are in principle not to be regarded as true to scale; rather, some elements, such as for example layers, components and regions, may be shown with exaggerated thicknesses or large dimensions for better representation or for better understanding.

DETAILED DESCRIPTION OF ILLUSTRATIVE EMBODIMENTS

Figure 1A:
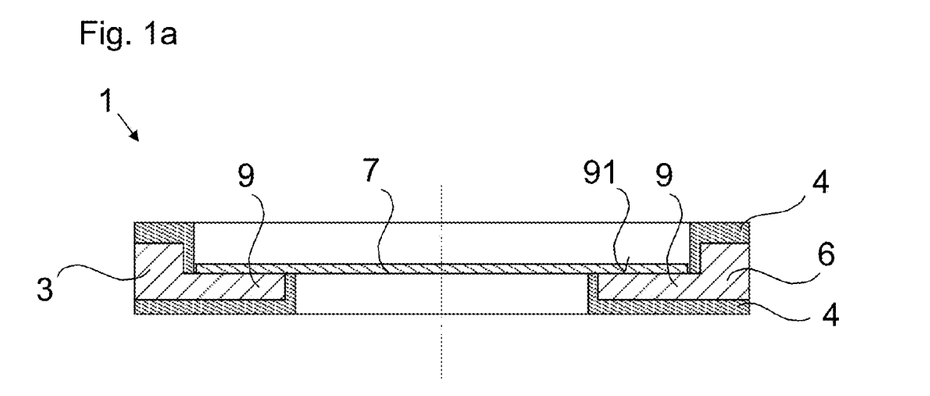
FIG. 1a shows a device for a radiation detector according to an exemplary embodiment, the device being formed as a window mount.

In FIG. 1a, a device 1 for a radiation detector is represented in a sectional view. The device 1 comprises a main body 3, for example with a circular extent in plan view. Alternatively, the main body 3 may also have a polygonal extent, for example rectangular or square, or an elliptical extent. The main body 3 also comprises a material G or consists of the material G.

In the exemplary embodiment shown, the device 1 is configured as a window mount 6, the main body 3 having a projection 9, which preferably protrudes inwards into a free space defined by the main body 3. The inside free space may be designed for the primary radiation that is to be detected to pass through the device. The primary radiation may, for example, have an energy of 10 keV.

In the exemplary embodiment shown, the projection 9 is formed as a peripheral, inwardly protruding projection. Alternatively, the projection 9 may also have a number of inwardly protruding, for example finger-shaped, portions. The projection 9 has a fastening region 91, which serves as a supporting surface for a window 7 and serves for the fastening of the window 7 to the window mount 6. The window 7 is connected to the window mount 6 in a fixed and preferably gastight manner, for example brazed. The window is also preferably configured in such a way that it is opaque to visible light, but more transparent to x-ray radiation. The main body 3 of the window mount 6 is at least partially provided with a coating 4, which comprises one or more layers. The fastening region 91, which serves for the fastening of the window 7, is free from the coating 4.

For example, the material G of the main body 3 of the device 1 may comprise iron or consist of iron, the primary fluorescence line or $K_\alpha$ line of which lies at 6.4 keV. An adequately thick first layer, arranged on the main body 3, of chromium, the absorption edge of which lies at 6.0 keV, can then absorb this radiation emitted by the main body 3 almost completely.

TABLE 1

| Cr layer thickness $d_{Cr}$ as a multiple of the absorption length $\lambda_{Cr}$ | Cr layer thickness $d_{Cr}$ (μm) | Cr absorption length $\lambda_{Cr}$ at 6.4 keV (μm) | Degree of radiation absorbed |
|---|---|---|---|
| $\lambda_{Cr}$ | 3.154 | 3.154 | 63.21% |
| $2\lambda_{Cr}$ | 6.308 | 3.154 | 86.47% |
| $3\lambda_{Cr}$ | 9.462 | 3.154 | 95.02% |
| $6\lambda_{Cr}$ | 18.924 | 3.154 | 99.75% |

Table 1 clearly shows by way of example the degree of radiation absorbed in percent for various layer thicknesses, which can be determined by the equation already introduced further above in the general part of the description $(1-\exp(-d_{Cr}/\lambda_{Cr}(6.4\text{ keV}))$.

Figure 1B:
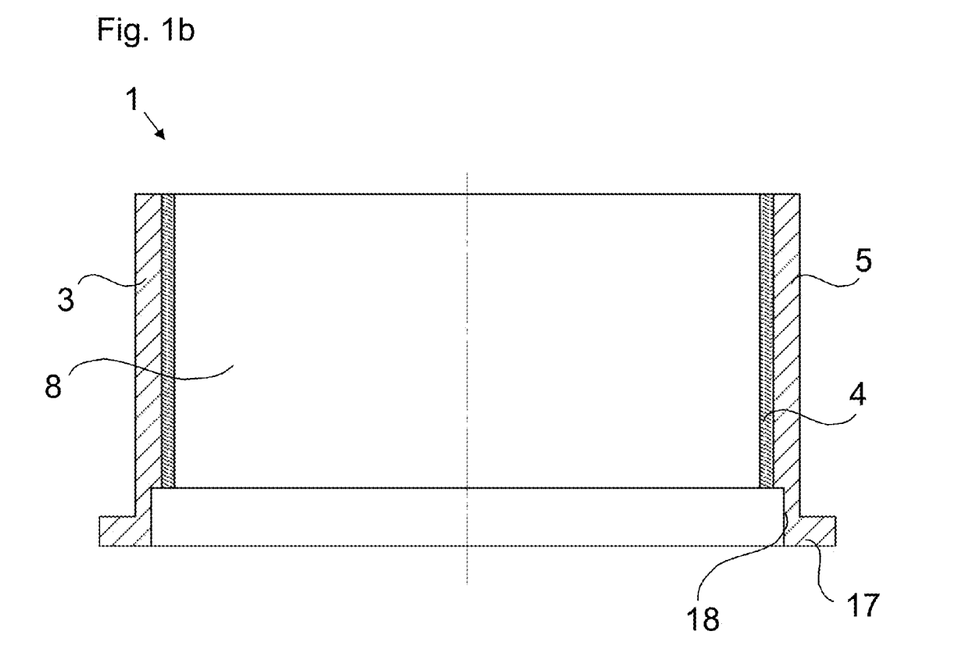
FIG. 1b shows a device for a radiation detector according to a further exemplary embodiment, the device being formed as a cap.

In FIG. 1b, a further exemplary embodiment of a device 1 is shown in a lateral sectional view, the device being formed as a protective cap 5 for a radiation detector. The protective cap 5 comprises a main body 3, which comprises a material G. Furthermore, the protective cap 5 defines a cavity 8.

The main body 3 of the protective cap 5 has exposed inner surfaces, which are at least partially provided with a coating 4.

In a lower region 17, the protective cap 5 also has a recess 18. In this region 17, the cap 5 may be connected to a base 15 of a radiation detector 2 (see FIG. 3). In addition, the protective cap 5 is suitable for allowing the window mount 6 from FIG. 1a to be connected to the protective cap 5.

Figure 2:
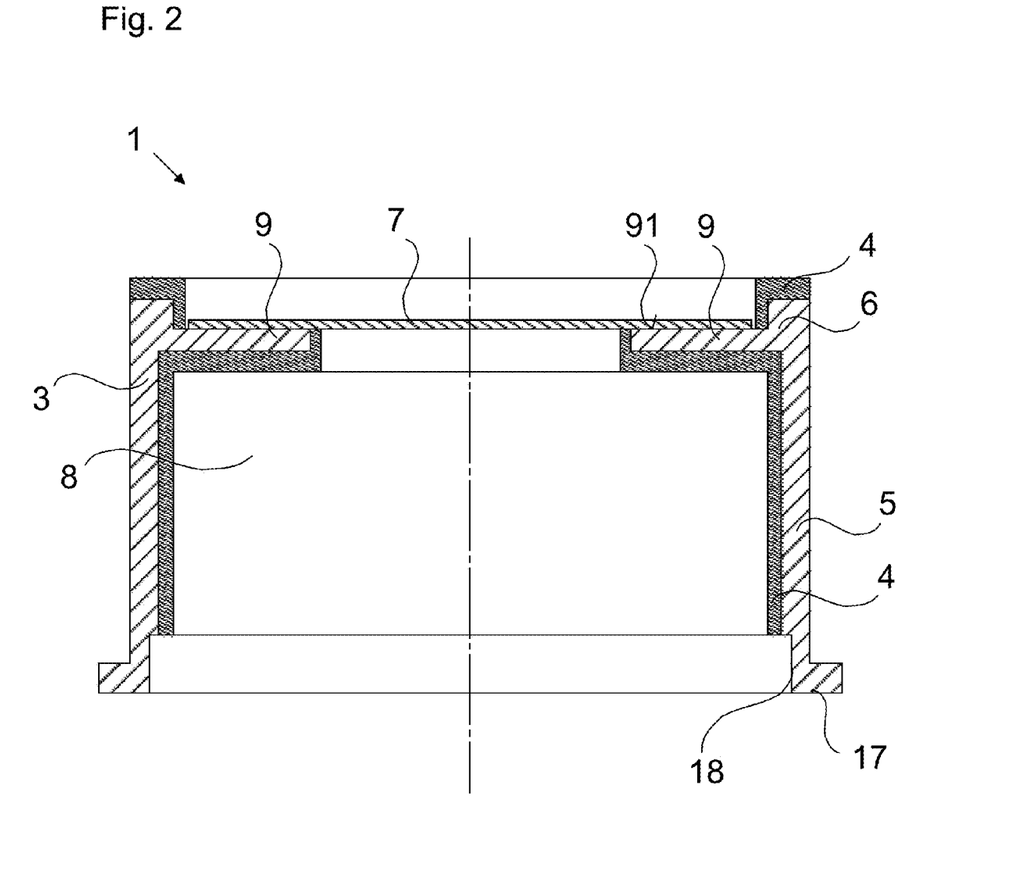
FIG. 2 shows a device for a radiation detector according to a further exemplary embodiment, the device being formed as a cap with an integrated window mount.

FIG. 2 shows the device 1, the window mount 6 being integrated in the protective cap 5. The protective cap 5 and the window mount 6 consequently have a common main body 3, which is at least partially provided with the coating 4. The protective cap 5 is, in particular, coated on exposed inner surfaces, a recess 18 in a lower region 17 of the cap 5 being free from the coating. The upper region of the device 1, which is formed as a window mount 6, is provided with the coating 4 with the exception of fastening regions 91 of the projection 9, at which the window 7 is fastened. Alternatively, the recess 18 may also be provided with the coating 4.

The considerations set out here may apply to all of the elements mentioned—the protective cap, the window mount, the protective cap with the window mount fastened to it or integrated in the cap.

Figure 3:
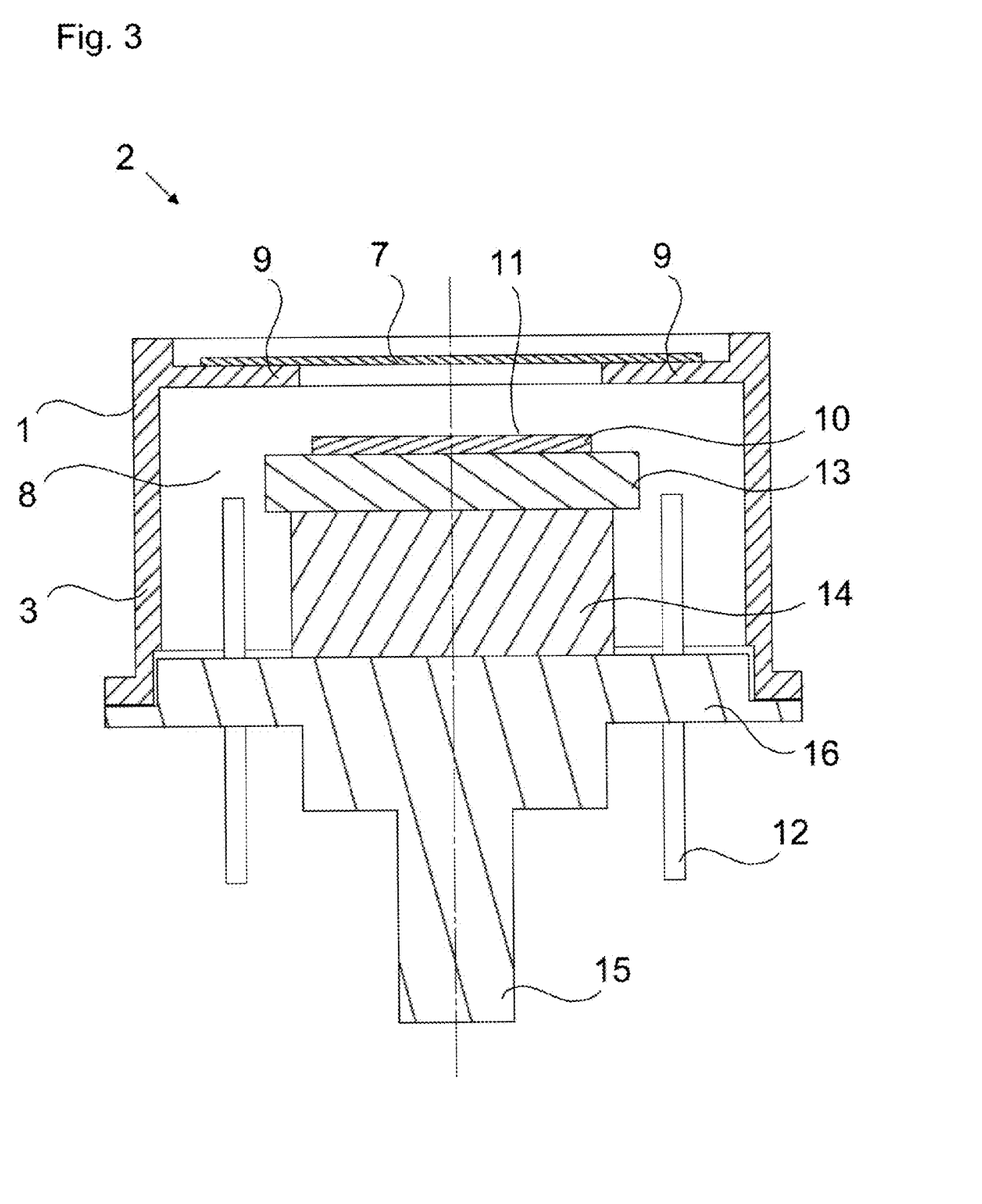
FIG. 3 shows a radiation detector with a cap and a window mount according to a further exemplary embodiment.

In FIG. 3, a radiation detector 2 is shown in a lateral sectional view. The radiation detector 2 has the device 1 from FIG. 2, the device 1 being shown without the coating 4, and the protective cap 5 and the window mount 6 being integrated here in a component merely by way of example. Furthermore, the radiation detector 2 has a detector element 10, which in the exemplary embodiment shown is configured by way of example as a detector chip with a detection area 11. The detection element 10 is fastened on a carrier 13. Furthermore, the radiation detector 2 has a thermoelectric cooler 14, a base 15, a baseplate 16 and contact pins 12, which are fastened to the baseplate 16 and are connected to the detection element 10 in an electrically conducting manner, for example by way of bonding wires (not represented). The contact pins 12 serve as signal and control terminals.

Furthermore, the protective cap 5, the window mount 6, the window 7 and the baseplate 16 or the base 15 form a cavity 8, which may be closed in a gastight manner, and which is preferably evacuated or filled with shielding gas.

The detection element 10 is particularly suitable for detecting an incident primary radiation. The detection element 10 generates a signal when radiation in the range of sensitivity of the detection element 10 enters the detection element 10 through the detection area 11. This signal can be detected by way of the contact pins 12.

If no external shielding is used, it is not possible however to avoid the situation where the incident radiation to be detected reaches not only the detector element 10 but also the protective cap 5 and the window mount 6, which surround the detector element. As a consequence, photons or ionizing particles may induce in the cap 5 or the window mount 6 x-ray fluorescence radiation, which is likewise detected by the detector element 10, and consequently falsifies the measurement result.

By means of a device 1 provided with a coating according to one of the exemplary embodiments described here, such an undesired x-ray fluorescence radiation can be effectively minimized by an x-ray fluorescence radiation that is produced in the main body 3 of the device 1 or in a layer of the coating 4 being absorbed for the most part in a layer of the coating 4 lying thereover.

In many applications it is the case that incident radiation is incident not only perpendicularly to the detection area 11 of the radiation detector 2, but also obliquely or laterally. This is the case, for example, if a further radiation source irradiates a sample laterally of the radiation detector 2. If a suitable shielding is absent, the material G of the protective cap 5 may be excited and picked up by the detector 2 as an interfering signal. In order to prevent this, the protective cap 5 may be provided at least on the inner side with the coating 4. Preferably, however, the lower region of the cap 5, in which the cap 5 is connected to the base 15, is free from the coating 4. As a result, it can be ensured that the connection between the cap 5 and the base 15 is stable.

Figure 4:
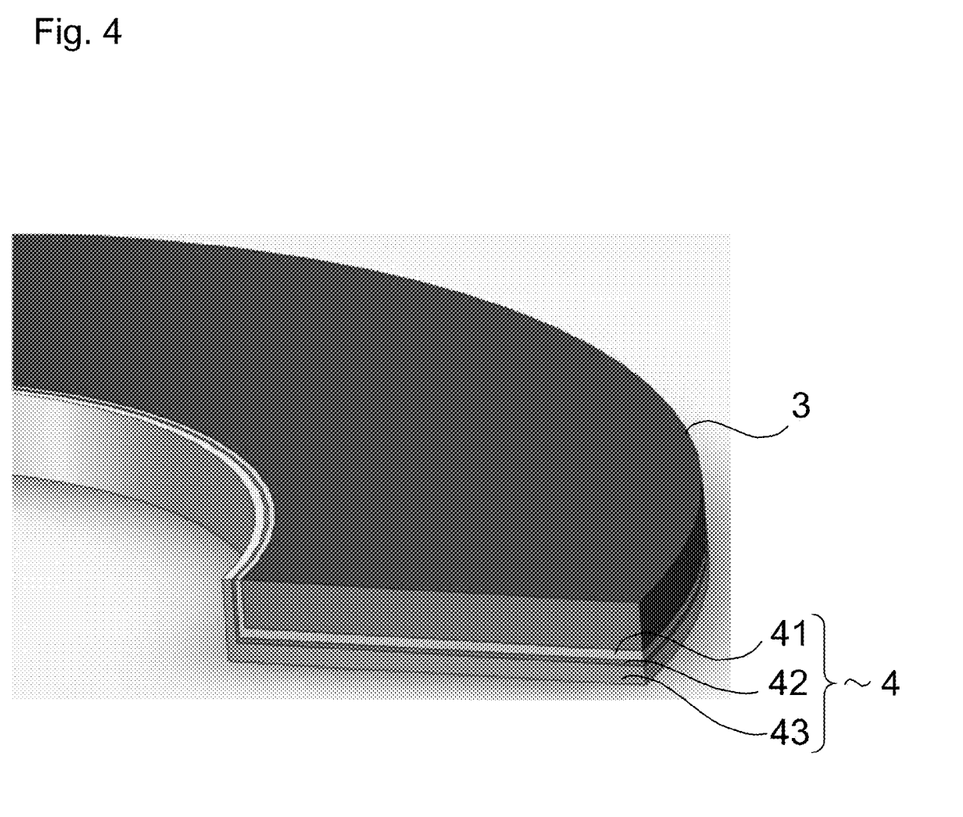
FIG. 4 shows a schematic representation of a coating of the device according to a further exemplary embodiment.

FIG. 4 clearly shows by way of example an exemplary embodiment of a coating 4, arranged on the main body 3 of the device 1 according to one of the preceding examples, in a schematic representation. The main body 3 comprises the material nickel. The coating 4 comprises a first layer 41, a second layer 42 and a third layer 43. The first layer 41 comprises chromium with a purity of 99.9%, the second layer 42 titanium with a purity of 99.9% and the third layer 43 aluminium with a purity of 99.9%. Furthermore, the first layer 41 has a thickness of about 25 µm, the second layer 42 a thickness of about 17 µm and the third layer 43 a thickness of about 65 µm. Undesired x-ray fluorescence radiation can be suppressed efficiently by such a multilayer system, by it being possible for an x-ray fluorescence radiation that is produced in the main body or in a layer to be at least partially absorbed by a layer respectively lying thereover.

Figure 5:
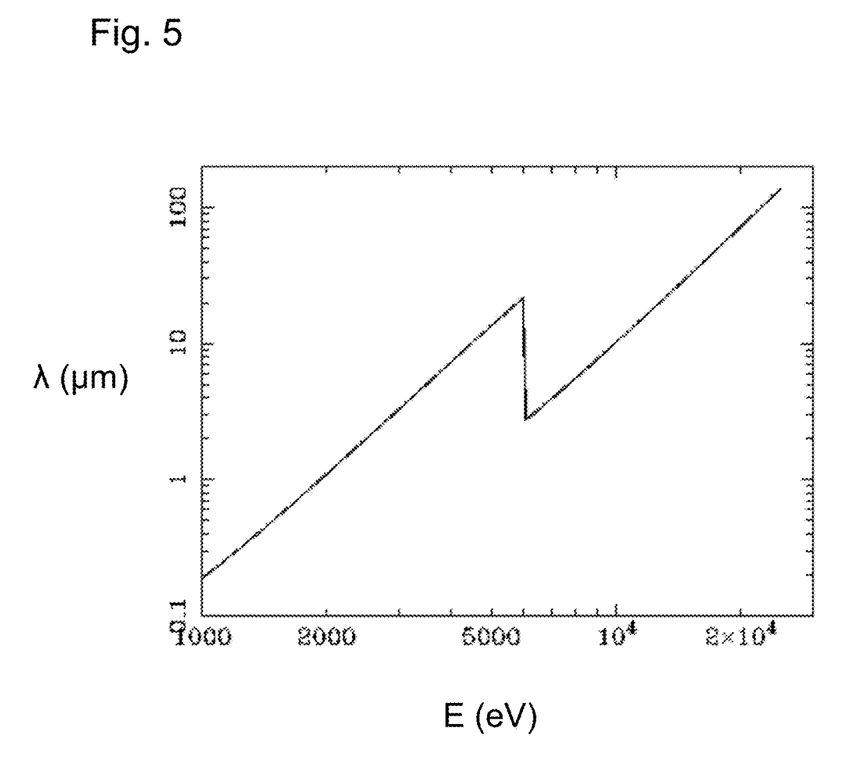
FIG. 5 shows a representation of an absorption edge of the chemical element chromium.

In FIG. 5, an absorption edge of chromium is represented by way of example, the excitation energy E of the incident radiation being plotted in eV on the x axis and the absorption length λ(E) being plotted in µm on the y axis. The absorption edge lies at about 6 keV and is characterized by a steep, abrupt drop of the absorption length, from approximately 20 µm to approximately 3 µm when there is a rise in the excitation energy of just a few hundred eV. At greater energies, the absorption length increases again from the minimum value that it assumed in the region of the edge.

Figure 6:
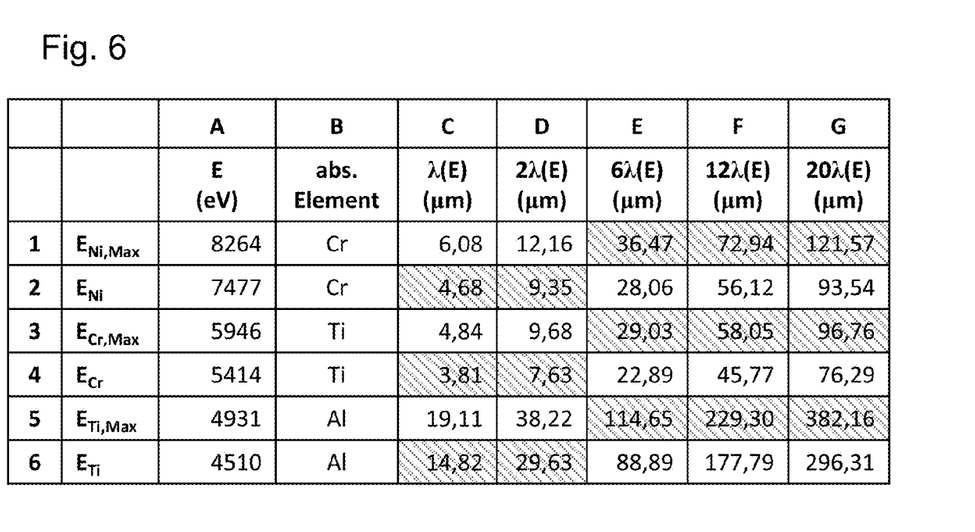
FIG. 6 shows a table representing the absorption lengths of various chemical elements by way of example.

In FIG. 6, a further exemplary embodiment of a multilayer system is represented by means of a table with the rows 1 to 6 and the columns A to G. The multilayer system comprises a main body, which comprises nickel, a first layer of chromium arranged on the main body, a second layer of titanium arranged on the first layer, and a third layer of aluminium arranged on the second layer.

In rows 1 to 6 of the table, the maximum energy $E_{Ni,Max}$ of nickel, the energy $E_{Ni}$ of the primary nickel line, the maximum energy $E_{Cr,Max}$ of chromium, the energy $E_{Cr}$ of the primary chromium line, the maximum energy $E_{Ti,Max}$ of titanium and the energy $E_{Ti}$ of the primary titanium line are represented one after the other. In column A, the energy is given in eV, in column B the respective absorbing element is given, in column C the associated, energy-dependent absorption length λ(E) is given in µm, in column D twice the absorption length 2λ(E), in column E six times the absorption length 6λ(E), in column F 12 times the absorption length 12λ(E), and in column G 20 times the absorption length 20λ(E) is given in µm, the values that are respectively relevant for the procedure described above of suppressing interfering x-ray fluorescence radiation being provided with background shading. Columns C and D may be used for determining the lower limits, i.e., the minimum layer thickness of the respective layer, and columns E to G may be used for determining the upper limits, i.e., the maximum layer thickness of the respective layer. In order for example to meet the initially mentioned condition $2\lambda_{A,i}(E_{A,i-1}) < d_{A,i} < 12\lambda_{A,i}(E_{A,i-1; Max})$, the chromium layer, for example, would have to be at least 9.35 µm and at most 72.94 µm thick. Undesired x-ray fluorescence radiation can also be successfully suppressed efficiently by a multilayer system described by means of the table from FIG. 5.

The invention is not restricted by the description on the basis of the exemplary embodiments to these embodiments but comprises each novel feature and any combination of features. This includes in particular any combination of features in the patent claims, even if this feature or this combination itself is not explicitly specified in the patent claims or exemplary embodiments.

What is claimed is:

1. A device for a radiation detector, comprising:
   a main body, comprising a material G; and
   a coating overlying at least a portion of the main body, the coating including a first layer that comprises a material $A_1$;
   wherein the material G can be excited by a primary radiation impinging on the coating, so that it produces an x-ray fluorescence radiation with an x-ray fluorescence spectrum, which has a maximum $M_G$ at an energy $E_G$;
   wherein at an energy $E_1$, the material $A_1$ has an absorption edge;
   wherein the material $A_1$ is chosen such that the following relationships apply: $E_1 < E_G$ and $E_G - E_1 \leq 4$ keV; and
   wherein the device is formed as a window mount and the main body has a projection for fastening a window.

2. The device according to claim 1,
   wherein the first layer has a thickness $d_{A,1}$;
   wherein the material $A_1$ has at the energy $E_G$ an absorption length $\lambda_{A,1}(E_G)$; and
   wherein the thickness $d_{A,1}$ is chosen such that $d_{A,1} > \lambda_{A,1}(E_G)$, where $\lambda_{A,1}$ is the energy-dependent absorption length of the material $A_1$.

3. The device according to claim 2, wherein $d_{A,1} > 2\lambda_{A,1}(E_G)$.

4. The device according to claim 2, wherein the thickness $d_{A,1}$ is chosen such that $d_{A,1} < 12\lambda_{A,1}(E_{G; Max})$, where $E_{G; Max}$ is the greatest energy, at which the x-ray fluorescence spectrum of the material G has a maximum.

5. The device according to claim 1, wherein the material G is a chemical element and the material $A_1$ is a chemical element, the atomic number of the element $A_1$ being less than the atomic number of the element G.

6. The device according to claim 1, wherein the coating has a number i of layers, each layer i respectively comprising a material $A_i$, and having a thickness $d_{A,i}$, where $i \geq 2$
   wherein the ith layer is arranged directly on the (i−1)th layer;
   wherein each layer i comprises a material $A_i$ which is different from the material $A_{i-1}$ of the layer lying thereunder; and
   wherein the relationship $\lambda_{A,i}(E_{A,i-1}) < d_{A,i} < 12\lambda_{A,i}(E_{A,i-1; Max})$ applies, where $\lambda_{A,i}$ is the energy-dependent absorption length of the material $A_i$;
   wherein the x-ray fluorescence spectrum of the material $A_{i-1}$ has a maximum at an energy $E_{A,i-1}$; and
   wherein $E_{A,i-1; Max}$ is the greatest energy, at which the x-ray fluorescence spectrum of the material $A_{i-1}$ has a maximum.

7. The device according to claim 6, wherein $2 \leq i \leq 10$.

8. The device according to claim 6, wherein
each material $A_i$ is a chemical element $B_i$,
each chemical element $B_i$ has an atomic number; and
the atomic number of the chemical element $B_i$ is less than the atomic number of the chemical element $B_{i-1}$.

9. The device according to claim 1, wherein the material G of the main body and the material of one or more layers of the coating respectively comprise elements with an atomic number greater than 10.

10. The device according to claim 1, wherein the material G of the main body and the material of one or more layers of the coating respectively comprise elements with a purity greater than 99.0%.

11. The device according to claim 1, wherein the coating has at least two layers, the layer of the coating that is furthest away from the main body comprising an element with an atomic number less than 10 and a purity less than 99.0%.

12. The device according to claim 1, wherein the primary radiation is an x-ray radiation.

13. The device according to claim 1, wherein at least part of a surface of the projection is free from the coating.

14. The device according to claim 1, wherein the device is formed as a cap for a radiation detector and defines a cavity, the cavity having exposed inner surfaces that are at least partially provided with the coating.

15. The device according to claim 14, wherein a window mount with at least one fastening region for the fastening of a window is provided in the cap, the fastening region being free from the coating, and regions that are adjacent to the fastening region being provided with the coating.

16. A radiation detector comprising:
a device according to claim 1, and
a detector element, configured to detect the primary radiation.

17. The radiation detector according to claim 16, wherein the coating comprises a plurality of layers, wherein the layer of the coating that is furthest away from the main body comprises a material with an x-ray fluorescence spectrum that has a maximum at an energy that lies outside an energy range that can be detected by the detector element.

18. The radiation detector according to claim 16, further comprising a window transparent to the primary radiation, wherein the window is fastened to the device and comprises a material that corresponds to the material of the layer of the coating that is applied to the device and is furthest away from the main body.

19. A device for a radiation detector, comprising:
a main body, comprising a material G; and
a coating overlying at least a portion of the main body, the coating including a first layer that comprises a material $A_1$;
wherein the material G can be excited by a primary radiation impinging on the coating, so that it produces an x-ray fluorescence radiation with an x-ray fluorescence spectrum, which has a maximum $M_G$ at an energy $E_G$;
wherein at an energy $E_1$, the material $A_1$ has an absorption edge;
wherein the material $A_1$ is chosen such that the following relationships apply: $E_1 < E_G$ and $E_G - E_1 \le 4$ keV; and
wherein the device is formed as a cap for a radiation detector and defines a cavity, the cavity having exposed inner surfaces that are at least partially provided with the coating.

20. A device for a radiation detector, comprising:
a main body, comprising a material G; and
a coating overlying at least a portion of the main body, the coating including a first layer that comprises a material $A_1$;
wherein the material G can be excited by a primary radiation impinging on the coating, so that it produces an x-ray fluorescence radiation with an x-ray fluorescence spectrum, which has a maximum $M_G$ at an energy $E_G$;
wherein at an energy $E_1$, the material $A_1$ has an absorption edge;
wherein the material $A_1$ is chosen such that the following relationships apply: $E_1 < E_G$ and $E_G - E_1 \le 4$ keV;
wherein the first layer has a thickness $d_{A,1}$;
wherein the material $A_1$ has at the energy $E_G$ an absorption length $\lambda_{A,1}(E_G)$; and
wherein the thickness $d_{A,1}$ is chosen such that $d_{A,1} > \lambda_{A,1}(E_G)$, where $\lambda_{A,1}$ is the energy-dependent absorption length of the material $A_1$; and
wherein the thickness $d_{A,1}$ is chosen such that $d_{A,1} < 12\lambda_{A,1}(E_{G;Max})$, where $E_{G;Max}$ is the greatest energy, at which the x-ray fluorescence spectrum of the material G has a maximum.

21. A device for a radiation detector, comprising:
a main body, comprising a material G;
a coating overlying at least a portion of the main body, the coating including a first layer that comprises a material $A_1$;
wherein the material G can be excited by a primary radiation impinging on the coating, so that it produces an x-ray fluorescence radiation with an x-ray fluorescence spectrum, which has a maximum $M_G$ at an energy $E_G$;
wherein at an energy $E_1$, the material $A_1$ has an absorption edge; and
wherein the material $A_1$ is chosen such that the following relationships apply: $E_1 < E_G$ and $E_G - E_1 \le 4$ keV;
wherein the coating has a number i of layers, each layer i respectively comprising a material $A_i$ and having a thickness $d_{A,i}$, where $i \ge 2$
wherein the ith layer is arranged directly on the (i−1)th layer;
wherein each layer i comprises a material $A_i$, which is different from the material $A_{i-1}$ of the layer lying thereunder;
wherein the relationship $\lambda_{A,i}(E_{A,i-1}) < d_{A,i} < 12\lambda_{A,i}(E_{A,i-1;Max})$ applies, where $\lambda_{A,i}$ is the energy-dependent absorption length of the material $A_i$;
wherein the x-ray fluorescence spectrum of the material $A_{i-1}$ has a maximum at an energy $E_{A,i-1}$; and
wherein $E_{A,i-1;Max}$ is the greatest energy, at which the x-ray fluorescence spectrum of the material $A_{i-1}$ has a maximum.

22. A radiation detector comprising:
a device;
a detector element, configured to detect the primary radiation impinging on the device; and
a window transparent to the primary radiation, wherein the window is fastened to the device;
wherein the device comprises a main body and a coating overlying at least a portion of the main body;
wherein the main body of the device comprises a material G;
wherein the coating includes a first layer that comprises a material $A_1$;
wherein the material G can be excited by a primary radiation impinging on the coating, so that it produces an x-ray fluorescence radiation with an x-ray fluorescence spectrum, which has a maximum $M_G$ at an energy $E_G$;

wherein at an energy $E_1$, the material $A_1$ has an absorption edge;
wherein the material $A_1$ is chosen such that the following relationships apply: $E_1 < E_G$ and $E_G - E_1 \leq 4$ keV; and
wherein the window comprises a material that corresponds to the material of the layer of the coating that is applied to the device and is furthest away from the main body.

* * * * *